(12) United States Patent
Sagel et al.

(10) Patent No.: US 8,524,200 B2
(45) Date of Patent: Sep. 3, 2013

(54) TOOTH WHITENING PRODUCTS

(75) Inventors: Paul Albert Sagel, Mason, OH (US);
Lan Ngoc Nguyen, West Chester, OH (US); Randy P. Washington, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1254 days.

(21) Appl. No.: 10/820,590

(22) Filed: Apr. 8, 2004

(65) Prior Publication Data
US 2005/0019275 A1 Jan. 27, 2005

Related U.S. Application Data

(63) Continuation-in-part of application No. 10/659,100, filed on Sep. 10, 2003, now abandoned.

(60) Provisional application No. 60/409,862, filed on Sep. 11, 2002.

(51) Int. Cl.
*A61K 6/00* (2006.01)
*A61K 8/22* (2006.01)
*A61Q 11/00* (2006.01)

(52) U.S. Cl.
USPC .............. 424/53; 424/49; 424/401; 433/216; 433/217.1

(58) Field of Classification Search
USPC ................. 424/49, 53, 401; 433/216, 217.1
See application file for complete search history.

(56) References Cited

U.S. PATENT DOCUMENTS

| 5,891,453 | A | * | 4/1999 | Sagel et al. | ................... | 424/401 |
| 2002/0187111 | A1 | * | 12/2002 | Xu et al. | ......................... | 424/53 |
| 2002/0187181 | A1 | * | 12/2002 | Godbey et al. | ................ | 424/443 |
| 2003/0194382 | A1 | * | 10/2003 | Chang et al. | .................... | 424/53 |

OTHER PUBLICATIONS

DC Chemical Co., Ltd., http://www.oci.co.kr/english/product/p_petr/p_petr8.htmpages 1-10, 2001.*
Dow Chemicals, http://www.dow.com/polyox/intro.htm pp. 1-2, Aug. 2002.*
"Mixture." The American Heritage® Dictionary of the English Language, Fourth Edition. Houghton Mifflin Company, 2004. Answers.com May 20, 2008. http://www.answers.com/topic/mixture page 1.*

\* cited by examiner

*Primary Examiner* — Lezah Roberts
(74) *Attorney, Agent, or Firm* — Armina E. Stricklin; Carrie A. Morgan; James A. Vago

(57) ABSTRACT

A tooth whitening product is provided. The tooth whitening product has a backing layer and a tooth whitening composition. The tooth whitening composition includes first and second water soluble polymers, water, and a tooth whitening agent, wherein the first water soluble polymer is polyethelene oxide and the second water soluble polymer is polyvinyl alcohol.

18 Claims, 3 Drawing Sheets

TOOTH WHITENING PRODUCTS

CROSS REFERENCE TO RELATED APPLICATIONS

This application is a continuation-in-part of application Ser. No. 10/659,100, filed Sep. 10, 2003, which claims the benefit of U.S. Provisional Application No. 60/409,862, filed Sep. 11, 2003, the substances of which are incorporated herein by reference.

TECHNICAL FIELD OF INVENTION

The present invention relates to products for whitening teeth, and, more particularly, to products for whitening teeth that have a whitening agent incorporated therein.

BACKGROUND OF THE INVENTION

Tooth whitening has become very popular over the past few years. More and more consumers are choosing to whiten their teeth. Options for tooth whitening include toothpastes, mouthrinses, chewing gums, in-office bleaching, and most commonly tooth whitening solutions used with a tray obtained either over-the-counter or from a dentist. Tooth whitening products using a strip of material in combination with a chemical whitening active are known in the art. For example, U.S. Pat. No. 6,419,906, the substance of which is incorporated herein by reference, describes a tooth whitening product comprising a strip of material formed from a water hydratable polymer and a tooth whitening agent. While these whitening products may function for their intended purpose, there is continuing desire to improve the handling and aesthetics of these tooth whitening products.

SUMMARY OF THE INVENTION

A tooth whitening product is provided. The tooth whitening product has a backing layer and a tooth whitening composition. The tooth whitening composition includes first and second water soluble polymers, water, and a tooth whitening agent, wherein the first water soluble polymer is polyethelene oxide and the second water soluble polymer is polyvinyl alcohol.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION OF THE EMBODIMENTS

Figure 1:
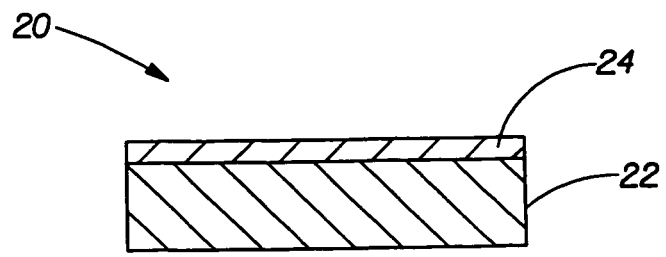
FIG. 1 is a cross-sectional side view of tooth whitening product made in accordance with the present invention, wherein a coating of a tooth whitening agent has been applied to a film.

All patents and patent applications referenced herein are hereby incorporated by reference herein. All weight percentages herein refer to the tooth whitening composition after processing (e.g., after drying, cooling, curing, extrusion, or casting). Reference will now be made in detail to embodiments of the invention, examples of which are illustrated in the accompanying drawings wherein like numerals indicate the same elements throughout the views and wherein elements having the same two last digits (e.g., 20 and 120) connote similar elements. The present invention is directed to tooth whitening products comprising a tooth whitening composition including a tooth whitening or bleaching agent and one or more water soluble polymers and, optionally, water, and a plasticizer. In another embodiment, the invention is directed to a tooth bleaching composition comprising a tooth whitening agent and a polyethylene oxide polymer and a polyvinyl alcohol polymer. As used herein, the phrase "water soluble" preferably means a compound or composition whose solubility in water is greater than 5 wt %, preferably greater than 10 wt %, or more preferably greater than 15 wt % when measured in water at 20C without the aid of pH adjusting agents, including solutes which are require temperatures greater than 20C to solubilize in water but which still have the above-stated weight percentages when the solution is cooled to 20C. Solubility is determined by centrifugation at 15,000 RPM for 30 minutes without separation. Solutions containing a water soluble polymer may be opaque, translucent or clear. More preferably, "water soluble" means a compound or composition whose solubility in water is greater than 5 wt %, preferably greater than 10 wt %, or more preferably greater than 15 wt % when first mixed in water at 20C without the aid of pH adjusting agents. The water soluble polymers are also preferably water hydratable. As used herein, the phrase "water hydratable" is intended to refer to a compound or composition that absorbs water. While the present invention will be described herein with respect to these films or strips, it is contemplated that the present invention can be used with other tooth whitening products, such as dental trays. Water soluble polymers, which are also water hydratable, suitable for use with the present invention include ethylene oxide polymers, homopolymers or mixtures of ethylene oxide polymers of varying molecular weight ranging from about 10,000 Daltons and up to about 10,000,000 Daltons and preferably in the range of about 100,000 to about 1,500,000 Daltons. Such ethylene oxide polymers are commercially available from various sources. Polyethylene oxide in the molecular weight range of 10,000 to 1,000,000 Daltons is available from the Union Carbide Company under the tradename "Polyox". Other suitable polymers include polypropylene oxide, cross-linked polyacrylic acid, e.g., Carbopol, linear polyacrylic acid, polyvinyl alcohol, sodium alginate, methyl methacrylate, xanthan gum, pectin, pullulan, guar gum, agar, polyvinyl pyrolidone (PVP), carrageanan, celluloses (e.g., hydroxypropylcellulose, hydroxyethyl cellulose, hydroxypropylmethyl cellulose and hydroxymethyl cellulose), polyethylene oxide polypropylene oxide copolymers (e.g., poloxamer), microcrystalline cellulose, polyvinyl pyrolidone polyvinyl acetate copolymers, poly vinyl ester-methyl_copolymers, polyoxyethelene-polyoxypropylene block copolymer, and mixtures thereof. While the thickness of the film may vary, as described more fully hereafter, the film may have a thickness between about 0.1 micrometer and about 1500 micrometer (μm). The tooth whitening composition may be provided as a standalone film or may be applied to, coated on, or otherwise provided with a backing layer or strip of material. The backing layer can be provided as a single layer or as a laminate formed from a plurality of layers, such as any combination of a foam, mesh, or a strip of material. The backing layer can be water permeable, water impermeable, or partially water permeable. The backing layer can be continuous or discontinuous (i.e., formed from a plurality of discrete segments). Examples of some suitable backing layers are described in U.S. Pat. Nos. 5,891,453; 5,989,569; and 2004/0005277.

Hydration of the water soluble polymer by saliva in the oral cavity allows release (e.g., solubilizes, diffuses, or mobilizes) of the whitening agent incorporated in the polymer matrix. The whitening agent releases from the tooth whitening product to the tooth surfaces to which the tooth whitening composition is applied. Whitening or bleaching agents suitable for the practice of the present invention include peroxides, metal chlorites, perborates, percarbonates, peroxyacids, persulfates, and combinations thereof. Suitable peroxide compounds include hydrogen peroxide, urea peroxide, calcium peroxide, and mixtures thereof. Suitable metal chlorites include calcium chlorite, barium chlorite, magnesium chlorite, lithium chlorite, sodium chlorite, and potassium chlorite. The preferred chlorite is sodium chlorite. A preferred percarbonate is sodium percarbonate. Preferred persulfates are oxones.

Optionally, the water soluble polymer may be mixed with a plasticizer. Suitable plasticizers include glycols such as propylene glycol, polyethylene glycol, methoxypolyethylene glycol, polyhydric alcohols such as glycerin sorbitol, and xylitol, and glycerol esters such as glycerol triacetate. Glycerin can be used as well as propylene glycol or polyethylene glycol such as is available from Union Carbide Corporation as their series of Carbowaxes that range in molecular weight from 200 to 600 Daltons. Other plasticizers include cellulose esters, sebacate esters, castor oil, tricresyl phosphate, phthalate, adipate, ethyl citrate, ethanolamine, and oligosaccharides.

Optionally, any of the tooth whitening compositions described herein may further include an amount of water. The amount of water that is present may be varied by the amount of drying or curing that occurs. The embodiments of the present may include greater than about 2%, or about 4%, or about 6% or about 10% and/or less than about 90%, or about 40%, or about 30% of water by weight percent of the tooth whitening composition after drying.

In one embodiment of the present invention, a tooth whitening product 20 comprises a water soluble polymeric film 22 and a solid whitening agent that has been applied as a coating 24 to one side of the water soluble polymeric film 22, as shown in FIG. 1. The solid tooth whitening agent can be applied while the film is still tacky or after the film has dried, cured, or cooled. Application of the tooth whitening agent in this manner reduces exposure of the tooth whitening agent to any water that may have been used as a solvent in forming the film and also reduces the amount of contact between the water soluble polymer and the tooth whitening agent in comparison to a water hydratable film having a tooth whitening agent dispersed there throughout. In addition, this embodiment has an increased concentration of the tooth whitening agent at the surface that is applied to the teeth. Such a coating can also assist in the diffusion of the tooth whitening agent toward the tooth surface since the coating is directly adjacent and/or in contact with the tooth surface during use. Suitable solid tooth whitening agents that can be applied to one side of a water soluble polymeric film include carbimide peroxide, calcium peroxide, percarbonate, sodium percarbonate, perborates, persulfates, and mixtures thereof. These tooth whitening agents can be sprayed, applied by gravure printing, mist grinding, drop powdering, and other processes known in the art.

The coating of the solid tooth whitening agent can cover all or a portion of the water soluble polymeric film. The thickness of the coating can be greater than about 0.001 microns, or greater than about 0.005 microns, or greater than about 0.01 microns or greater than about 0.05 microns, or greater than about 0.1 microns, or greater than about 1 micron, or greater than 5 microns and/or less than about 100 microns, or less than about 50 microns, or less than about 10 microns, or less than about 1 micron. The dose per unit area of the tooth whitening agent is at least about 0.001 $mg/cm^2$, or at least about 0.005 $mg/cm^2$, or at least about 0.01 $mg/cm^2$, or at least about 0.05 $mg/cm^2$, or at least about 0.1 $mg/cm^2$, or at least about 1 $mg/cm^2$, or at least about 10 $mg/cm^2$, or at least about 100 $mg/cm^2$ and/or less than about 500 $mg/cm^2$, or less than about 250 $mg/cm^2$, or less than about 100 $mg/cm^2$, or less than about 10 $mg/cm^2$. Other materials can be mixed with the solid tooth whitening agent or applied sequentially before or after application of the solid tooth whitening agent. For example, binders, adherents, starches, sweeteners and flavorants, colorants (e.g., to aid in distinguishing the active side of the strip from the non-active side), release agents (e.g., talc powder, manitol powder, lecithin, corn oil, bees wax, silica, calcium monostearate, glycerol monostearate, alkali salts of long chain fatty acids) which facilitate release of the tooth whitening composition from a surface such as a casting plate, pH adjusting agents, including alkalizing agents or acidifying agents, surfactants (e.g., polysorbate 80 and glyceryl oleate), and other oral care actives can be applied as part of the application step. While the solid tooth whitening agent can be applied in a dry form, it is contemplated that a solvent could be used with the tooth whitening agent during application. In one embodiment, a solvent that solubilizes both the water soluble polymer and the tooth whitening agent can be employed when applying the tooth whitening agent to the surface of the water soluble film. In this process, the tooth whitening is solubilized in the solvent and then applied to the surface of the water soluble film so that the tooth whitening agent is dispersed at least partly within the film as the solvent can solubilize a portion of the film. Alternatively, the solvent may only solublize the tooth whitening agent, in which case a discrete coating would be formed on one side of the film after solvent evaporation or removal. Suitable solvents could include solvents that can solubilize the tooth whitening agent at a given temperature but which do not solubilize the water soluble polymer at that temperature. Some examples include Cellosolve acetate, anisole, 1,4 dioxane, ethyl acetate, ethylenediamine, dimethyl Cellosolve, Cellosolve solvent, alcohols such as ethanol, methanol, or iso-propanol, Carbitol solvent, n-butanol, cuyl Cellosolve, n-butyl acetate, 2-propanol, and methyl Cellosolve, and mixtures thereof.

The water soluble polymeric film 22 can be prepared using a conventional extrusion, calendaring, pressing or solvent casting processes. For example, to prepare a film by solvent casting polyethylene oxide, the ethylene oxide polymer or mixture of polymers is dissolved in a sufficient amount of a solvent which is compatible with the polymer. Examples of suitable solvents include water, alcohols, acetone, ethyl acetate or mixtures thereof. After a solution has been formed, a plasticizer is added with stirring, and heat is applied if necessary to aid dissolution, until a clear and homogeneous solution has been formed, followed by the addition of the whitening agent and any other ingredients such as flavors. The solution is coated onto a suitable carrier material and dried to form a film. The carrier material must have a surface properties that allow the polymer solution to spread evenly across the intended carrier width without soaking in to form a destructive bond between the two substrates. Examples of suitable carrier materials include glass, stainless steel, teflon, polyethylene-impregnated kraft paper. The solution can also be cast onto the previously described backing layers, a pouch or a portion of a package for the tooth whitening composition. Drying of the film may be carried out in a high-temperature air-bath using a drying oven, drying tunnel, vacuum drier, or any other suitable drying equipment, after which the tooth whitening agent can be sprayed onto the film.

In another embodiment of the present invention, the efficacy and/or stability of the tooth whitening agent can be increased by forming the water soluble film with a solvent other than water so that the tooth whitening agent does not come into contact with water during the formation process and there is no residual water left in the film post manufacture. As used herein, the term "stability" is intended to refer to the propensity of a material to maintain its original concentration or structure over a fixed period of time. As used herein, the term "efficacy" is intended to refer to the amount of tooth whitening per unit time. In one process, the water soluble polymer and the tooth whitening agent are mixed and then fed to an extruder whose screw, through mechanical action, melts the water-hydatratable polymer. The melted polymer is then extruded into a film to be formed into the tooth whitening product.

The efficacy of the tooth whitening agent can also be increased by reducing the amount of water soluble polymer that forms the film. In one embodiment, the water soluble polymer film further comprises water insoluble organic and/or inorganic additives to reduce the amount of the water soluble polymer so that solubilization of the tooth whitening agent is maximized during use. Suitable water insoluble organic materials include polyolefins (e.g., polyethylene, polypropylene, polybutenes, polyisoprenes, and copolymers thereof) and polyester. Suitable water insoluble inorganic materials include calcium phosphate, calcium pyrophosphate, and titanium dioxide, and silica. The water insoluble additives can comprise at least about 10%, or at least about 20%, or at least about 30% and/or less than about 90%, or less than about 80%, or less than about 70%, or less than about 50% or less than about 40%, or less than about 30% by weight of the film. In these embodiments, the amount of the water soluble polymer is at least about 5%, or at least about 10%, or at least about 20%, or at least about 30% and/or less than about 90%, or less than about 80%, or less than about 70% by weight of the film. The water insoluble additives can be ground prior to incorporation into the film. In one embodiment, the average particle size of the water insoluble additives is at least about 1 micron, or at least about 20 microns, or at least about 25 microns and/or less than about 100 microns, or less than about 50 microns, or less than about 25 microns, or less than about 10 microns. In addition to decreasing the amount of water soluble polymer that is available to react with the tooth whitening agent, the concentration of tooth whitening agent available at the surface of the tooth can be increased during hydration, because more water is available to solubilize the tooth whitening agent rather than hydrating or otherwise solubilizing the water soluble polymer. The tooth whitening agent can be admixed with the water soluble polymer as described in U.S. Pat. No. 6,419,906 or coated onto the film as previously described.

Figure 2:
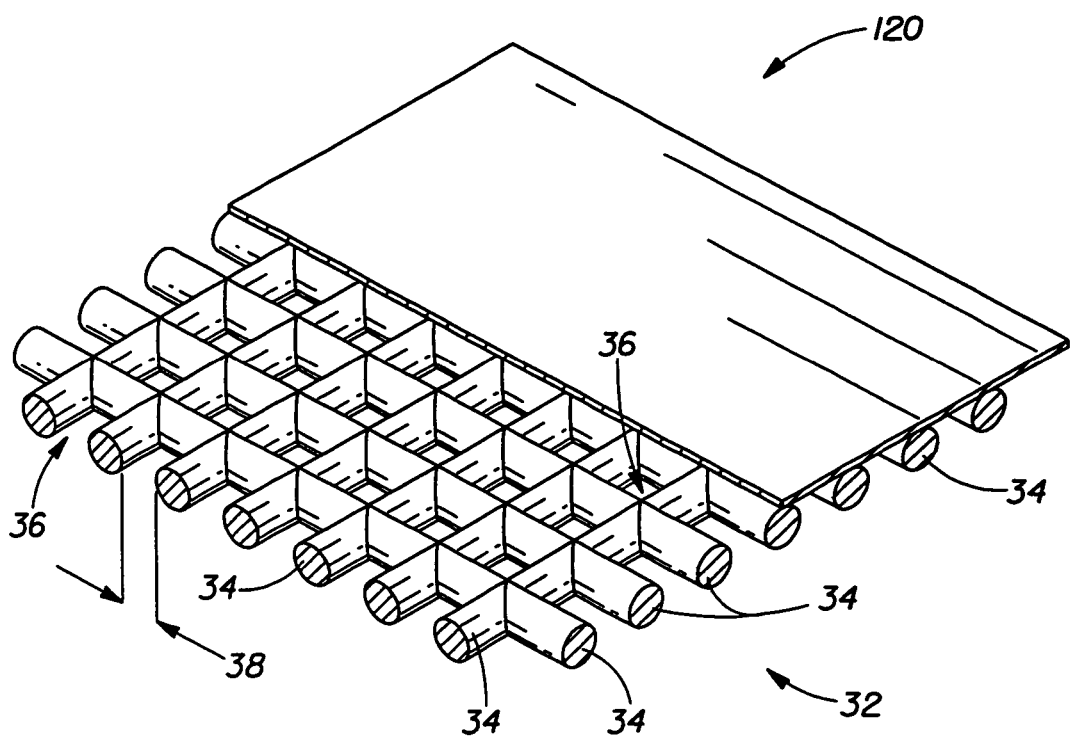
FIG. 2 is a perspective view of another embodiment of a tooth whitening product of the present invention, wherein the tooth whitening product comprises a web and a coating that completely bridges the void spaces of the web and wherein a portion of the coating has been removed to reveal features there below.

In yet another embodiment of the present invention, a web, scrim, or mesh is incorporated in the tooth whitening product to improve the hydration of the film. The web, scrim, or mesh can be formed from fibers that are aligned in random or repeating geometric patterns. Referring to FIG. 2, a tooth whitening product 120 comprising a web 32 is illustrated. The web 32 is formed from fibers 34 that are arranged in a repeating geometric pattern. The fibers can be formed from one or more water insoluble, water soluble, or water hydratable polymers and may have a tooth whitening agent incorporated therein. If the fibers are formed from water insoluble materials, the web may function in a manner similar to the previously described films that incorporate water insoluble materials. The fibers are arranged in a manner to provide void spaces 36 between the fibers. The void spaces can facilitate hydration of the web 32 and therefore solubilization of the tooth whitening agent. The void spaces can vary in size or have a substantially constant size over the web. For example, the void spaces might be smaller in one region and larger in another region depending upon the desired rate of hydration. The fibers 34 can have a diameter of at least about 1 micron, or at least about 5 microns, or at least about 10 microns, or at least about 20 microns, or at least about 50 microns and/or less than about 200 microns, or less than about 100 microns, or less than about 50 microns, or less than about 20 microns. The spacing 38 between fibers is at least about 1 micron, or at least about 5 microns, or at least about 10 microns, or at least about 20 microns, or at least about 50 microns, or at least about 1 mm, or at least about 1.5 mm and/or less than about 5 mm, or less than about 2.5 mm, or less than about 1.5 mm, or less than about 50 microns.

Figure 3:
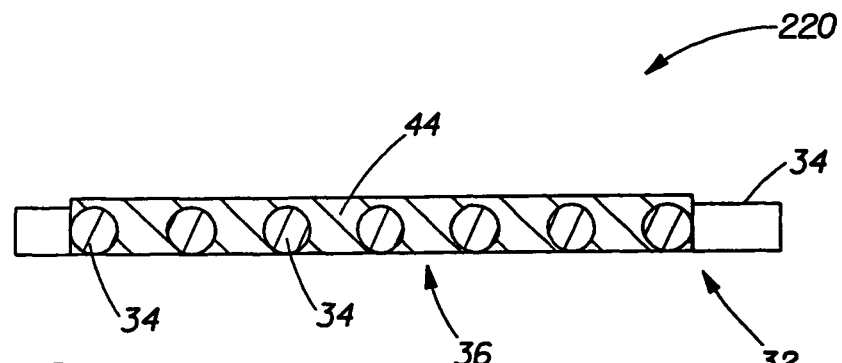
FIG. 3 is a cross-sectional side view of the tooth whitening product of FIG. 2, wherein the void spaces are shown as partially filled.
Figure 4:
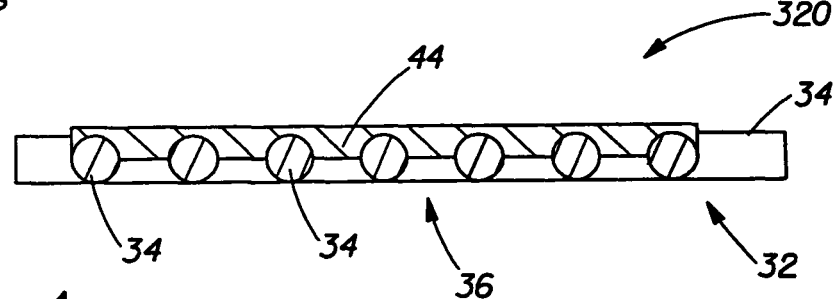
FIG. 4 is a cross-sectional side view of the tooth whitening product of FIG. 2, wherein the void spaces are shown as completely filled.
Figure 5:
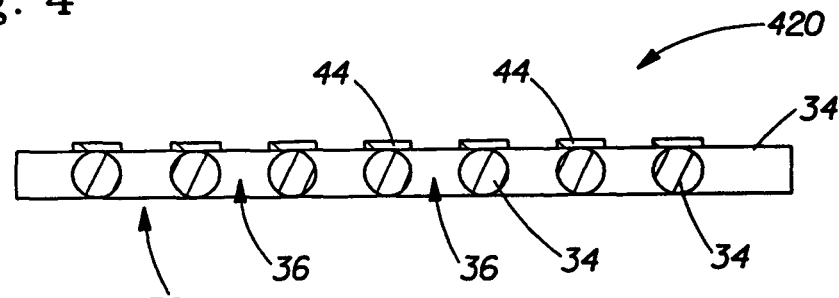
FIG. 5 is a perspective view of another embodiment of a tooth whitening product of the present invention, wherein the tooth whitening product comprises a web and a coating that partially bridges the void spaces of the web.
Figure 6:
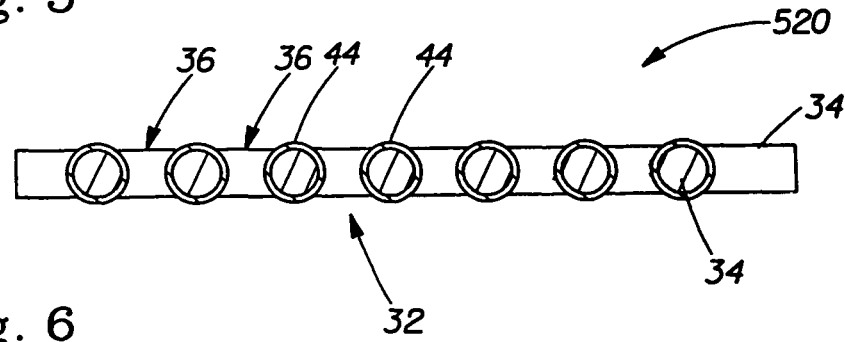
FIG. 6 is a perspective view of another embodiment of a tooth whitening product of the present invention, wherein the tooth whitening product comprises a web and a coating that does not bridge the void spaces of the web.

In an alternate embodiment, a tooth whitening product 220, shown in FIG. 3, comprises a web 32 having a coating or layer 44 applied thereto. The web 32 can be formed a water soluble, water insoluble, or water hydratable polymer or other material, such as other polymers (e.g., polypropylene, polyethylene, etc.) and cellulose. The fibers 34 of the web 32 can be arranged in a random or repeating pattern. The coating 44 comprises a water soluble polymer and a tooth whitening agent. Other materials can be included in the coating, such as a plasticizer, water, water insoluble additives, etc. The coating can bridge the void spaces 36 such that a substantially solid layer is formed on web 32. The coating might completely fill the void spaces as shown in FIG. 3 or partially fill the void spaces as shown in FIG. 4 with respect to tooth whitening product 320. When the void spaces are partially filled, the pocket 50 that is formed can facilitate hydration of the web and therefore solubilization and release of the tooth whitening agent. Alternatively, the coating 44 can only partially bridge the void spaces, as shown in FIG. 5 for the tooth whitening product 420. In yet another embodiment, a coating 44 does not bridge the void spaces 36 of web 32 but merely coats the fibers 34, either wholly or partially, as shown by way of example in FIG. 6 for the tooth whitening product 520.

The concentration of the tooth whitening agent within the coating and/or the fibers and the amount of water soluble polymer can be varied within these web embodiments depending upon the extent to which the coating bridges the void spaces and/or coats the fibers and based upon the desired rate of solibilization of the tooth whitening agent. As will be appreciated, any combination of completely filling the voids, partially filling the voids, partially bridging the voids, and coating the fibers can be provided in one embodiment.

Figure 7:
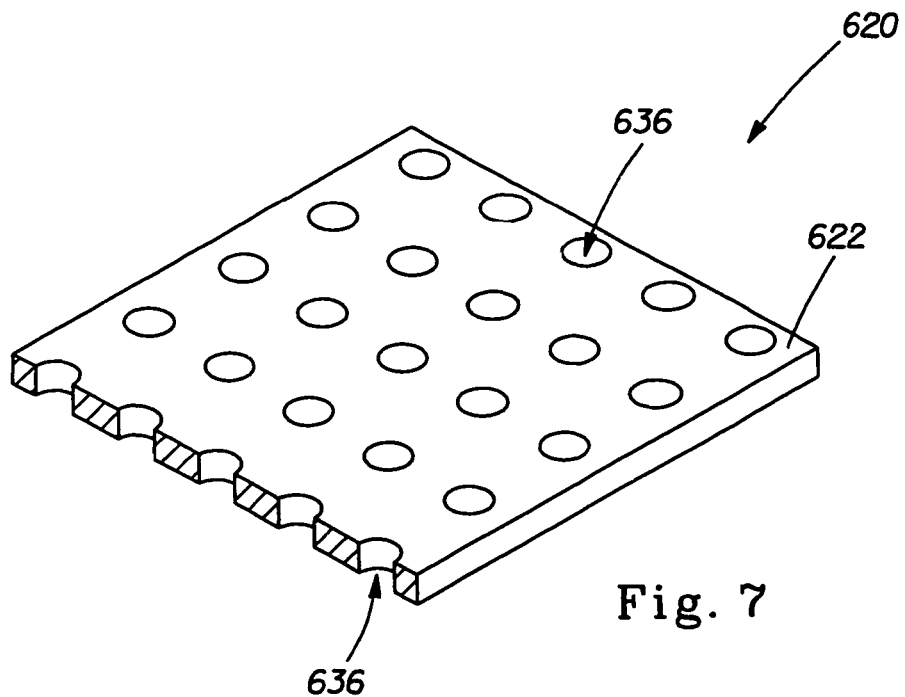
FIG. 7 is a cross-sectional side view of another embodiment of a tooth whitening product of the present invention that comprises a perforated film.

In a related embodiment, a perforated film without a distinct web or scrim might be provided, as shown in FIG. 7. In the tooth whitening product 620, a single or multilayer film might be provided comprising a water soluble polymer, a tooth whitening agent, a plasticizer, and optionally water. The film can be perforated after it has dried or cured. The void spaces, holes, or apertures 630 that are formed during the perforation process can pass completely through the thickness of the film or might only partially penetrate the film thickness. The void spaces 636 can have the same dimensions as previously described with respect the void spaces of the web. The void spaces 636 can be provided in a random or repeating pattern and vary in size and shape as previously described. Further, this embodiment can include a coating of a tooth whitening agent as previously described or other features of the embodiments discussed above.

Figure 8:
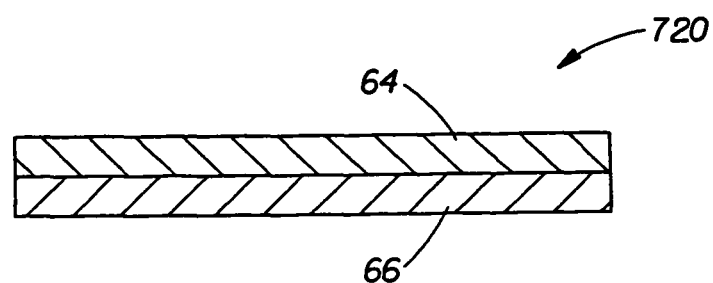
FIG. 8 is a perspective view of another embodiment of a tooth whitening product of the present invention that comprises a first layer and a second layer.

In another embodiment of the present invention, a tooth whitening product 720 is provided in the form of a laminated film as shown in FIG. 8. The laminated film comprises two or more layers comprising water hydratable polymers; A first layer 64, which is to be applied to the teeth, further comprises a tooth whitening agent. The water hydratable polymer comprises at least about 1%, or at least about 10%, or at least about 20% and/or less than about 90%, or less than about 70%, or less than about 50% by weight of the first layer. The tooth whitening agent comprises at least about 1%, or at least about 10%, or at least about 15% and/or less than about 70%, or less than about 60%, or less than about 50% by weight of the first layer. The balance of the first layer can comprise water or other materials, such as the previously described water insoluble additives or a plasticizer. The second layer 66, which is positioned adjacent the lips and/or cheeks during use, preferably does not comprise a tooth whitening agent. The water hydratable polymer of the second layer 66 comprises at least about 20%, or at least about 30%, or at least about 40% and/or less than about 100%, or less than about 90%, or less than about 80% by weight of the second layer. A plasticizer comprises at least about 0.1%, or at least about 1%, or at least about 2% and/or less than about 40%, or less than about 30%, or less than about 20% by weight of the second layer. The balance of the second layer 66 can comprise other materials, such as water, water insoluble additives, or oral care actives other than a tooth whitening agent. Examples of other oral care actives suitable for use with the present invention include phosphates (e.g., pyrophosphates, polyphosphate, polyphosphonates, and mixtures thereof), fluoride ion sources, antimicrobial agent, anti-imflamatory agents, nutrients, and enzymes. These oral care actives are further described in U.S. Pat. No. 6,096,328 (and the patents cited therein), the substances of which are incorporated herein by reference. These other oral care actives could also be incorporated into a film comprising only a single layer and formed from a water-hydratable polymer (e.g., polyethyylene oxide) and a plasticizer, the basic formation of which is described in U.S. Pat. No. 6,419,906.

The composition of the first layer 64 and the second layer 66 of the tooth whitening product 720 can be adapted to provide different functionalities. For example, the first layer 64 might comprise less of the water hydratable polymer than the second layer 66 so that the first layer 64 hydrates more quickly thereby solubilizing the tooth whitening agent more quickly and more effectively (i.e., providing a greater concentration more quickly). The second layer can contain relatively more of the water hydratable polymer so that it functions as a barrier layer preventing diffusion of the solubilized tooth whitening agent away from a tooth while still permitting some hydration from the back side of the tooth whitening product. Also, since the second outer layer comprises more of the water soluble polymer, it will remain in a film-like state longer than the first layer 64 so that the tooth whitening agent will have a longer period of time in which to act upon the teeth. The absence of the tooth whitening agent from the second layer could also improve tissue tolerablity as a peroxide source would not be directly adjacent the soft tissue of the lips and cheeks. The tooth whitening product 720 can be formed by casting the first layer first followed by the second layer being cast on top of the first layer either before or after the first layer has dried or cured. The layers can be pressed together by rollers aligned so that there is nip of gap there between through which the first and second layers pass. The first and second layers can comprise the same water soluble polymer or distinct water soluble polymers.

In another aspect of the present invention, a film comprising a water soluble polymer and a tooth whitening agent is provided in a thin form and with an increased concentration of the tooth whitening agent. The thickness of the film is at least about 1 µm, or at least about 5 µm, or at least about 10 µm, or least about 15 µm and/or less than about 2 mm, or less than about 1 mm, or less than about 0.5 mm, or less than about 0.25 mm, or less than about 0.1 mm, or less than about 20 µm, or less than about 15 µm. The concentration of the tooth whitening agent is at least about 1%, or at least about 10% or at least about 15%, or at least about 20%, or least about 25% and/or less than about 70%, or less than about 60%, or less than about 50%, or less than about 40%, or less than about 30%. Surprisingly, these increased concentration levels of the tooth whitening agent can be utilized while still maintaining acceptable soft tissue tolerability without the need for cumbersome rubber dams or other artificial soft tissue barriers. As used herein, the phrase "artificial barrier" is intended to refer to any physical means that prevents or is intended to prevent a tooth whitening agent from migrating onto the soft tissue adjacent the teeth during a bleaching operation. Other artificial barriers can include light cured resins. As used herein, the phrase "soft tissue tolerability" is intended to refer to the degree to which a user experiences a sensation often described as burning or stinging or experiences irritation of the gingival tissues. This sensation can range from minor to severe. In addition, one or more layers, preferably without a tooth whitening agent, can be provided adjacent the previously described layer containing the tooth whitening agent.

In another embodiment, the tooth whitening composition comprises two or more water soluble polymers, a tooth whitening agent, and optionally a plasticizer, and/or water. The tooth whitening composition may be provided as a layer on a backing layer, as as a stand-alone film, or in other forms. In a preferred embodiment, the first water soluble polymer is a polyethylene oxide polymer and the second water soluble polymer is polyvinyl alcohol. The polyethylene oxide may have an average molecular weight greater than about 100,000, or about 200,000, or about 300,000, or about 600,000 and or less than about 10,000,000, or about 4,000,000, or about 1,500,000, or about 900,000. The tooth whitening composition may comprise greater than about 10%, or about 20%, or about 30% or about 40% and/or less than about 90%, or about 60%, or about 50% by weight of polyethylene oxide. The tooth whitening composition may comprise mixtures of polyethylene oxides have different average molecular weights. The tooth whitening composition may comprise greater than about 0.5%, or about 2%, or about 5% and/or less than about less than about 90% or about 50%, or about 20%, or about 15% or about 10% by weight of polyvinyl alcohol. The ratio of the first water soluble polymer to the second water soluble polymer is between about 10:90 and about 90:0.5 or between about 50:2 and about 30:20. The polyvinyl alcohol may have varying degrees of hydrolysis. The degree of hydrolysis signifies the extent of conversion of polyvinyl acetate to polyvinyl alcohol. A mixture of polyethylene oxide and polyvinyl alcohol will be more adhesive and less cohesive as the degree of hydrolysis of the polyvinyl alcohol increases. Thus, for the same amount of polyethylene oxide, less polyvinyl alcohol is required as the degree of hydrolysis of the polyvinyl alcohol increases in order to provide the same level of adhesiveness. The polyvinyl alcohol may be super hydrolyzed, fully hydrolyzed, intermediately hydrolyzed, or partially hydrolyzed. Typically, the range of hydrolysis, from partially hydrolyzed to super hydrolyzed, is between about 70% (partially hydrolyzed) and about 99.5% (super hydrolyzed). In one embodiment, the range of hydrolysis is greater than about 70%, or about 80%, or about 87% and/or less than about 99%, or about 95%, or about 91%. As used herein, the phrase "hydrolysis" is intended to refer to the level of hydrolysis of the raw material before manufacture of the tooth whitening composition. In another embodiment, the range of hydrolysis is between about 87% and about 91% and the amount of polyvinyl alcohol between about _5_% and about _50_% by weight of the tooth whitening composition. The tooth whitening composition may also optionally include a plasticizer. In one embodiment, the tooth whitening composition may comprise greater than about 1%, or about 10%, or about 20% and/or less than about 80%, or about 60%, or about 80% by weight of a plasticizer. A preferred plasticizer is polyethylene glycol. A more preferred plasticizer is a polyethylene glycol having a molecular weight between about 200 and about 9,000. The tooth whitening composition may also optionally include water at the same levels as previously discussed herein. The tooth whitening composition. The tooth whitening composition may include hydrogen peroxide greater than about 0.5%, or about 3%, or about 6% and/or less than about 40%, or about 20%, or about 10% by weight of the tooth whitening composition. The foregoing embodiments of a tooth whitening composition comprising two water soluble polymers may also incorporate aspects of any of the other embodiments described herein, such as a mesh or scrim, water insoluble organic or inorganic additives, perforations, etc.

Non-limiting examples of the foregoing embodiments incorporating a mixture of polyethylene oxide and polyvinyl alcohol are set forth below. It will be appreciated that these compositions may include additional ingredients or other ingredients may be substituted for those listed. Each example sets forth the tooth whitening composition formulation before drying and after drying.

EXAMPLE 1

| | Polyethylene oxide WSR-1105 (MW 900,000) | Polyvinyl alcohol Gohsenol GL-05S (86.5%-89%) | PEG 600 | Water | Hydrogen peroxide |
|---|---|---|---|---|---|
| % wt before drying | 6 | 2 | 6.5 | 82.5 | 3 |
| % wt after drying | 30 | 10 | 35 | 10 | 15 |

EXAMPLE 2

| | Polyethylene oxide WSR-205 (MW 600,000) | Polyvinyl alcohol Gohsenol NH-26 (99.4%) | PEG 600 | Water | Hydrogen peroxide |
|---|---|---|---|---|---|
| % wt before drying | 7.5 | 0.5 | 5 | 85 | 2 |
| % wt after drying | 40 | 2.5 | 25 | 22.5 | 10 |

EXAMPLE 3

| | Polyethylene oxide WRS-1105 (MW 900,000) | Polyvinyl alcohol Gohsenol KH-17 (78.5-81.5%) | PEG 600 | Water | Hydrogen peroxide |
|---|---|---|---|---|---|
| % wt before drying | 4 | 5 | 6 | 84 | 1 |
| % wt after drying | 20 | 25 | 30 | 19 | 6 |

EXAMPLE 4

| | Polyethylene oxide WSR-N750 (MW 300,000) | Polyvinyl alcohol Gohsenol GL-05S (86.5-89%) | PEG 600 | Water | Hydrogen peroxide |
|---|---|---|---|---|---|
| % wt before drying | 6.5 | 3 | 6 | 81.5 | 3 |
| % wt after drying | 34 | 15 | 30 | 6 | 15 |

Embodiments of the polyethylene oxide/polyvinyl alcohol mixtures of the present invention, including examples 1 to 4, can be made by preparing a first mixture comprising polyethylene oxide and a solvent, such as water, and a second mixture comprising polyvinyl alcohol and a solvent, such as water. It will be appreciated that a mixture of solvents might also be used herein. Both mixtures are separately stirred until both the polyethylene oxide and the polyvinyl alcohol are fully hydrated. The first and second mixtures are combined and a tooth whitening agent (e.g., hydrogen peroxide) and optionally a plasticizer (e.g., PEG 600) are added. This tooth whitening composition may be cast on a backing layer or a suitable drying surface. The tooth whitening composition is then dried until a desired amount of the solvent has been removed. The tooth whitening composition can be freeze dried or a drying tunnel incorporating radiant or convective heating can be used. In one embodiment, the tooth whitening composition can be dried in drying box using a nitrogen air mixture at room temperature at a flow rate between about 0.085 m$^3$/min and about 0.3 m$^3$/min. The drying time may be between about 15 minutes and about 2 hours or between about 20 minutes and about 60 minutes.

The above described embodiments of the present invention can be further combined with other layers such as a thin protective coating layer, e.g., of 10 nanometers (nm) to 500 microns (um) thickness or a backing layer formed from a strip of material. The coating material is applied in a sufficiently thin layer so as not to interfere with the flexibility of the film and to allow the whitening strip to conform to an arrangement of a row of teeth. The coating materials can be one or a combination of high molecular weight (that is, molecular weights greater than 1,000,000 Dalton) and include, ethyl cellulose, propyl cellulose, isopropyl cellulose, butyl cellulose, t-butyl cellulose, cellulose acetate, and derivatives of polyvinyl alcohol such as polyvinyl acetate and shellac.

The tooth whitening products of the present invention can be packaged in pouches as individual strips or a roll of film can be provided in a tape-like dispenser, wherein individuals strips can be cut from the roll for use in the oral cavity or the film can be provided with perforations or other frangible features to permit separation of predetermined length strips from the roll of film. Optionally, the tooth whitening products of the present invention can further include a release liner. The release liner can be formed from any material that exhibits less affinity for the film and/or web than the film or web exhibits for itself. The release liner can be formed from polymer films, paper, foils, woven, non-wovens, and other suitable materials known in the art. Optionally, the release liner can include a coating such as wax, silicone, Teflon®, fluoropolymers, etc. The films of the present invention can be formed directly on the release liner. The release liner can be cut to the desired size either before or after formation of the film thereupon. The tooth whitening products of the present invention can also be provided as liner for dental trays, such as those described in U.S. Pat. No. 5,098,303, wherein the strips are incorporated into the trough of the dental tray.

To use the tooth whitening products of the present invention, the film when applied to the teeth surface when hydrated by saliva in the oral cavity or prewetted by dipping the strip in water will adhere to the teeth in an appropriate manner. In this regard, the tooth whitening product is formed to have a width dimension suitable to cover a row of teeth (upper or lower). Therefore, the tooth whitening product may be applied to the upper set of teeth, or to the lower set of teeth either separately or simultaneously. The length dimension of the tooth whitening product is determined by the amount of coverage desired. In this regard, the number of teeth which it is desired to whiten will determine the dimensions of the product. For instance, it may be desired to only whiten the front teeth, which are most easily seen by others. Accordingly, the length of tooth whitening product can be reduced in this case, as compared to the case where it is desired to whiten all of the teeth. The duration of application of product to the teeth will depend upon the type and concentration of the tooth whitening agent, as well as the type and intensity of extrinsic or intrinsic stain.

The embodiments described herein were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A packaged tooth whitening product, comprising:
a backing layer; and
an adhesive layer of a water hydratable tooth whitening composition comprising first and second polymers, from about 10% to about 90% water, and a tooth whitening agent, wherein said first polymer is polyethylene oxide having an average molecular weight between about 300,000 and about 900,000 and said second polymer is polyvinyl alcohol.

2. The packaged tooth whitening product of claim 1, wherein the concentration of said first polymer is between about 10% and about 90% and said tooth whitening agent is between about 1% and about 40% by weight of said tooth whitening composition.

3. The packaged tooth whitening product of claim 1, wherein the concentration of said second polymer is between about 0.5% and about 50% by weight of said tooth whitening composition.

4. The packaged tooth whitening product of claim 1, wherein said tooth whitening composition further comprises a plasticizer having a concentration between about 1% and about 80% by weight of said tooth whitening composition.

5. The packaged tooth whitening product of claim 4, wherein said plasticizer is polyethylene glycol.

6. The packaged tooth whitening product of claim 1, wherein said polyvinyl alcohol has a hydrolysis between about 70% and about 91%.

7. The packaged tooth whitening product of claim 1, wherein said backing layer is a laminate.

8. The packaged tooth whitening product of claim 1, wherein said first polymer comprises a mixture of two or more polyethylene oxides and wherein said polyethylene oxides have different average molecular weights.

9. The packaged tooth whitening product of claim 1, wherein said tooth whitening agent is hydrogen peroxide.

10. The packaged tooth whitening product of claim 1, wherein said first and second polymers are water soluble.

11. The packaged tooth whitening product of claim 1, wherein the backing layer is water impermeable.

12. The packaged tooth whitening product of claim 1, wherein the backing layer is discontinuous.

13. The packaged tooth whitening product of claim 1, wherein the backing layer comprises a plurality of holes.

14. The packaged tooth whitening product of claim 13, wherein the tooth whitening composition comprises a plurality of holes.

15. The packaged tooth whitening product of claim 1, wherein the tooth whitening composition is formed by casting.

16. The packaged tooth whitening product of claim 1, wherein the layer of a tooth whitening composition is coextensive with the backing layer.

17. The packaged tooth whitening product of claim 1, wherein the backing layer is partially water permeable.

18. The packaged tooth whitening product of claim 1, wherein the tooth whitening product has a thickness less than 1 mm.

* * * * *